United States Patent [19]

Lambert et al.

[11] Patent Number: 4,888,415
[45] Date of Patent: Dec. 19, 1989

[54] GELONIN IMMUNOTOXIN

[75] Inventors: John M. Lambert; Walter A. Blättler, both of Brookline; Peter D. Senter, Boston, all of Mass.

[73] Assignee: Dana-Farber Cancer Institute, Inc., Boston, Mass.

[21] Appl. No.: 166,777

[22] Filed: Mar. 7, 1988

Related U.S. Application Data

[63] Continuation of Ser. No. 707,650, Mar. 4, 1985, abandoned.

[51] Int. Cl.$^4$ .......................... A61K 39/44; C07G 7/00
[52] U.S. Cl. .................................... 530/390; 530/387; 530/388; 530/389; 530/391; 530/396; 530/828; 424/85.91; 424/88; 514/2; 514/6; 514/8
[58] Field of Search ............... 530/370, 387, 388, 389, 530/390, 391, 396, 828; 514/2, 6, 8; 424/85.91, 88

[56] References Cited

U.S. PATENT DOCUMENTS

| | | | |
|---|---|---|---|
| 4,232,119 | 4/1980 | Carlsson et al. | 435/7 |
| 4,340,535 | 7/1982 | Voisin et al. | 530/388 |
| 4,363,758 | 12/1982 | Masuno et al. | 530/388 |
| 4,379,145 | 4/1983 | Masuno et al. | 514/21 |
| 4,450,154 | 5/1984 | Masuno et al | 530/388 |

FOREIGN PATENT DOCUMENTS 2382695 9/1978 France .................. 530/388

OTHER PUBLICATIONS

King et al, Biochem. vol. 17(8) 1978, pp. 1499-1506, "Preparation of Protein Conjugates via Intermolecular Disulfide Bone Formation".
Lambert et al, Biochem vol. 22, 1983, pp. 3913-3920, "Cross-Links Between Ribosomal Proteins of 30S Subunits in 70S Tight Couples and in 30S Subunits".
Blattler et al, Biochem. vol. 24(6) 1985, pp. 1517-1523, "New Heterobifunctional Protein Cross-Linking that Forms an Acid-Labile Link".
Lambert et al, J. BiolChem. vol. 260(22) Oct. 5, 1985, "Purified Immunotoxins that are Reactive with Human Lymphoid Cells".
Alagon et al, BioChem. vol. 19, pp. 4341-4345, 1980, "Activation of Polysaccharides with 2-imminothiolane and its use".
Traut et al., Biochemistry, vol. 12, pp. 3266-3273, (1973).
Jue et al., Biochemistry, vol. 17, pp. 5399-5406, (1978).
Schramm et al., Hoppe-Seyler's Z, Physiol. Chem. vol. 358, pp. 137–139, (1977).
Schramm et al., (1977) in Protein Crosslinking, (Friedman, M., Ed.) Part A, pp. 197-205, Plenum Publishing Corp., N.Y., NY.
Barbieri et al., Biochem J. vol. 23, pp. 55-59, 1982, "Purification and Partial Characterization of Another Form of the Antiviral Protein from the Seeds of Phytolacca americana L. (pokeweed)".
Stirpe et al., J. Biol. Chem., vol. 255, No. (14), pp. 6947–6953, 1980, "Gelonin, a New Inhibitor of Protein Synthesis, Non-Toxic to Intact Cells".
Thorpe et al., Eur. J. Biochem., vol. 116, 447–454, (1981).
Columbatti et al.; J. Immunol., vol. 131, 3091–3095, (1983).
Wiels et al., Cancer Research, vol. 44, 129–133 (1984).
Ramakrishnan et al., Cancer Research, vol. 44, 201–208 (1984).
Ritz et al., Nature, vol. 283, 583–585 (1980).
Woodbury et al., PNAS (USA), vol. 77, 2183–2186 (1980).
Herlyn et al., PNAS (USA), vol. 76, 1438–1442 (1979).
Seon et al., PNAS (USA), vol. 80, 845–849 (1983).
Barbieri et al., Cancer Surveys vol. 1, 489–520 (1982).
Olsnes et al., Molecular Action of Toxins and Viruses, (Cohen et al., eds), pp. 51–105, Elsevier, (1982).
Youle et al., PNAS (USA), vol. 77, 5483–5486, (1980).
Thorpe et al., Nature vol. 297, 594–596.
Vallera et al., Science, vol. 222, 512–515 (1983).
Masuho et al., J. Biochem., vol. 91, 1583–1591 (1982).

*Primary Examiner*—Robin Teskin
*Attorney, Agent, or Firm*—Fish & Richardson

[57] ABSTRACT

Immunotoxins having improved toxic activity have the composition

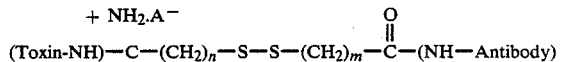

wherein Toxin-NH is a ribosome-inactivating protein containing no accessible sulfhydryl groups, n is an integer from 1 to 5, m is an integer from 1 to 5, and NH-Antibody is a monoclonal antibody specific to eucaryotic cells or antigens associated therewith. The immunotoxins are made by reacting the Toxin-NH with an iminothiolester salt to form a first conjugate, reacting the NH-Antibody with N-succinimidyl-3-(2-pyridyldithio) propionate to form a second conjugate, and reacting the two conjugates to form the immunotoxin.

10 Claims, No Drawings

GELONIN IMMUNOTOXIN

This case is a continuation of application No. 707,650 now abandoned.

The invention is concerned with reagents that deliver a toxic molecule, specifically to certain eucaryotic cells, such as parasites, and mammalian cells, preferably human cells, which results in specific destruction of these cells. The reagent can be called an immunotoxin and has three components: (a) a monoclonal antibody such as a murine or other mammalian monoclonal antibody, that binds highly specifically to certain eucaryotic cells, e.g. mammalian cells such as human, monkey and the like cells or to certain antigens associated therewith, (b) a ribosome-inactivating protein or toxin and (c) a linkage for the toxin to the antibody to permit the antibody to deliver the toxin to a specific target cell without separation or activation of the toxin prior to reaching the target cell in the environment which may be the body.

The possible use of antibodies as specific carriers of pharmacologic agents, such as toxins, has been the subject of rapidly developing research, owing much to the ability to produce pure, highly specific monoclonal antibodies using the hybridoma technology. Recently, monoclonal antibodies have been developed that recognize tumor-associated antigens as described by Ritz et al., Nature Vol. 283, 583–585 (1980); Woodbury et al., PNAS (USA) Vol. 77, 2183–2186 (1980); Herlyn et al., PNAS (USA) Vol. 76, 1438–1442 (1979); and Seon et al., PNAS (USA) Vol. 80, 845–849 (1983), and it is believed that such antibodies can be utilized to deliver toxic agents to the particular tumor cells in order to kill them selectively. The ribosome inactivating proteins described by Barbieri et al., Cancer Surveys Vol. 1, 489–520 (1982); and by Olsnes et al., Molecular Action of Toxins and Viruses, (Cohen et al., eds), pages 51–105, Elsevier, (1982) seem to be ideal toxic agents for this task. Most effort has been directed towards using ricin (extracted from castor beans; *Ricinus communis*) which consists of two non identical subunits (A and B chains) that are joined by a disulfide bond. Entry of the A chain into the cytoplasm of a cell results in the death of the cell by catalytic inactivation of its ribosomes. The B chain has the property of binding to cell surface carbohydrate moieties and seems to promote the uptake of the A-chain into cells.

Immunotoxins have previously been made by conjugating intact ricin to antibodies as described by Youle et al., PNAS (USA) Vol. 77, 5483–5486, (1980); Thorpe et al., Nature Vol. 297, 594–596; and by Vallera et al., Science Vol. 222, 512–515 (1983). Such immunotoxins exhibit specific toxicity only in the presence of lactose which at high concentration competes with the cell surface for the ricin B-chain binding sites. In vivo, these immunotoxins are expected to be non specifically toxic, as is ricin itself, and are therefore unlikely to be of therapeutic value, although they may have limited use in the in vitro treatment of bone marrow for transplantation. The free ricin A-chain, when completely separated from the B chain, shows $10^4$–$10^6$-fold less toxicity in vitro than intact ricin, owing to the inability of the free A chain to attach to the cell surface. When A chain was conjugated to antibodies, the resulting immunotoxins generally exhibited specific cytotoxicity towards those cells bearing the appropriate surface antigen. However, the development of the toxic effect was slow relative to ricin, which made it necessary to use prolonged incubation times. High toxicity was only demonstrated when the chemical linkage included a disulfide bond. There was little or no toxicity when the immunotoxin contained a chemically stable, non cleavable bond as described by Masuho et al., J. Biochem. Vol. 91, 1583–1591 (1982).

There is a class of ribosome inactivating proteins that have properties and characteristics similar to those of ricin A-chain alone. Gelonin and the three known pokeweed antiviral proteins (PAP) are examples of such proteins. They are basic proteins, of $M_r$ about 30,000 and are known to be extremely stable, they do not bind to cells and so are non toxic to intact cells (unless at very high concentrations), and they are safe to purify and manipulate without the extreme precautions necessary for work with ricin. Although immunotoxins have been made using gelonin and PAP, and in general they showed specific cytotoxicity of similar magnitude to immunotoxins prepared with ricin A chain as reported by Thorpe et al., Eur.J.Biochem., Vol. 116, 447–454 (1981); Columbatti et al., J.Immunol., Vol. 131, 3091–3095 (1983); Wiels et al., Cancer Research, Vol. 44, 129–133 (1984) and Ramakrishnan et al., Cancer Research, Vol. 44, 201–208 (1984), none was completely purified from non conjugated antibody. The presence of non-conjugated antibody may influence the results of cytotoxicity tests, for example, by blocking antigens or by saturating the internalization pathways, and this may account for the large variation in potency described for these immunotoxins.

Since gelonin and the PAP toxins, unlike the ricin A-chain, contain no accessible sulfhydryl groups it is necessary to first react them with a cross linking reagent, such as the usual one having the structure

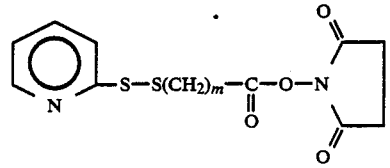

in which m is a integer from 1 to 5, such as N-succinimidyl 3-(2 pyridyldithio) propionate (SPDP), to give, after reduction of the disulfide bond of the dithiopyridyl group, a sulfhydryl-containing toxin conjugate which can then be covalently bonded to an analogousdithiopyridyl-containing antibody conjugate to form a disulfide containing linkage between the antibody and the toxin. It has been found that reaction of SPDP or the like with toxins of this class results in a marked and irreversible inactivation of the toxin, so that the final cross-linked toxin-antibody complex or immunotoxin displays markedly decreased toxic activity.

The present invention provides a covalently cross-linked complex between a toxin and an antibody, called an immunotoxin, of high activity by reacting a ribosome-inactivating protein containing no accessible sulfhydryl groups with an iminothiolester salt to form a sulfhydryl-containing conjugate, reacting a monoclonal antibody with SPDP to form a second, dithiopyridyl-containing conjugate, and covalently bonding the two conjugates to form a complex or immunotoxin in which the antibody is linked to the ribosome-inactivating protein or toxin through a disulfide linkage.

Any ribosome inactivating protein containing no accessible sulfhydryl groups can be employed as the toxin in the present invention, among which are gelonin from the seeds of *Gelonium multiflorum*, pokeweed antiviral protein from the seeds of *Phytolacca americana* (PAP-S) or from its leaves (PAP or PAP II), MCI from *Momordica charantia*, and the ribosome-inactivating protein from *Saponaria officinalis* L. Gelonin can be purified as described by Stirpe et al., J. Biol. Chem. Vol. 255, 6947-6953 (1980), PAP S purified as described by Barbieri et al. Biochem. J. Vol. 203, 55-59 (1982) and PAP and PAP II as described by Irvin et al. Arch. Biochem. Biophys. Vol. 200, 418-425 (1980), MCI can be purified as described by Bärbieri et al., Biochem.J., Vol. 186, 443-452 (1980), and the ribosome inactivating protein from *Saponaria officinalis* L as described by Stirpe et al., Biochem.J., Vol. 216, 617-625.

Among the iminothiolester salts which can be reacted with the toxin in the present invention are those having the structure:

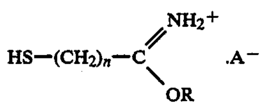

or 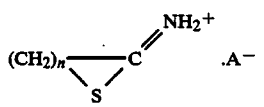 in which n is an integer from 1 to 5, R is an alkyl group having 1 to 5 carbon atoms, and A⁻is a water soluble anion such as chloride. Preferred ester salts include methyl 3 mercaptopropionimidate hydrochloride and 2-iminothiolane hydrochloride, the latter being the cyclized form of the 4 mercapto butyrimidate.

There can be employed as the antibody in the immunotoxin of the present invention any monoclonal antibody specific for eucaryotic cells, such as parasites and mammalian cells Of particular interest are antibodies specific for human tumor cells. Among suitable monoclonal antibodies are those specific for human T cells such as the anti-T12 of Reinherz U.S. Pat. No. 4,443,427 from hybridoma cell line ATCC No. 3513, the anti-$Ti_{IB}$ from hybridoma cell line ATCC No. HB 8213, and the anti-T3, -T4, -T11, and -T12 monoclonal antibodies available from Coulter Immunology as well as the monoclonal antibodies specific for the common acute lymphoblastic leukemia antigen such as the J5 described by Ritz et al., Nature, Vol. 283, 583-585 (1980) and the J13 described by Ritz et al. Biological Responses in Cancer (ed. Mihick), Vol. 1, 1-21 (1982), both of which are available from Coulter Immunology.

The reaction can be represented as follows:

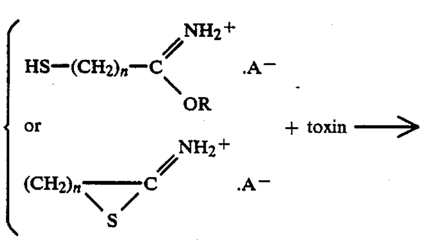

-continued

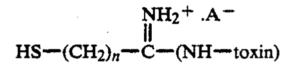

Conjugate 1

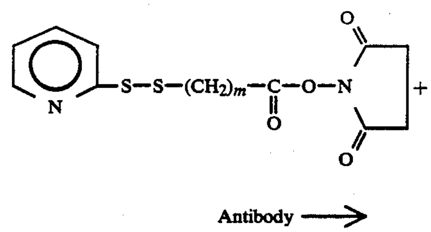

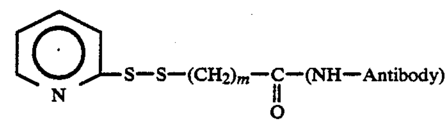

Conjugate 2

Conjugate 1 + Conjugate 2 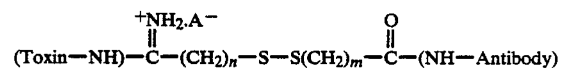 wherein n and m are integers from 1 to 5, R is an alkyl group having 1 to 5 carbon atoms, and A⁻is a non-toxic water soluble anion.

The reaction between the toxin and the iminothiolester salt can be carried out in aqueous medium such as any suitable buffer at about pH 6-9 at a temperature from about 0° C. to 50° C., preferably at about 0° C. The reaction is preferably conducted using an excess of the iminothiolester salt under an inert atmosphere to avoid oxidation of the sulfhydryl groups introduced into the toxin, and preferably leads to the introduction of 0.6 to 0.7 sulfhydryl group per toxin molecule during the course of 90 minutes or more. The reaction can be terminated by removing excess iminothiolester salt by gel filtration with suitable buffer.

The reaction between the monoclonal antibody and SDPD or the like is carried out in aqueous medium, such as any suitable buffer at about pH 6-9 at a temperature from 0° to 50° C., preferably from 25° to 35° C., using an excess of SDPD, for about 30 minutes or more. The reaction can be terminated by gel filtration in buffer or by dialysis against buffer at 0° to 40° C. The conjugate thus produced contains about 2 to 2.5 dithiopyridyl groups per antibody molecule.

The two conjugates prepared as described above can be reacted with each other to form the desired crosslinked immunotoxin simply by mixing with each other in an aqueous medium, e.g. any suitable buffer, at about pH 6-9 at a temperature of 0° to 50° C. Preferably the toxin conjugate is employed in excess, at a molar ratio of 2:1 to 8:1 of the antibody conjugate. The reaction leading to formation of the cross link containing a disulfide group is essentially complete in 20 hours or less. Any remaining free sulfhydryl groups can then be blocked, for example by adding iodoacetamide, and the reaction mixture incubated at 25° C. for an additional hour, at which point any non crosslinked toxin or toxin conjugate can be removed by gel filtration and/or by affinity chromatography.

The resultant purified immunotoxin exhibits a ribosome inactivating capacity nearly equal to that of the toxin employed as the starting material, as well as a specific binding capacity and avidity substantially unchanged from that of the monoclonal antibody starting material. The high level of cytotoxicity of the immunotoxins of the present invention makes them useful as assay reagents as well as therapeutic agents for the selective destruction of T-cells and/or certain leukemia cells, as in the in vitro treatment of bone marrow.

The following examples are intended to illustrate more clearly the nature of the present invention without acting as a limitation upon its scope.

EXAMPLE 1

An immunotoxin was prepared from monoclonal antibody J5 (anti CALLA) and gelonin.

The J5 antibody was purified from mouse ascites fluid by affinity chromatography on Protein A Sepharose CL-4B (Sigma Chem. Co., St. Louis, MO), as described by Ey et al, Immunochemistry, Vol. 15, 429–436 (1978). The antibody was further purified by ion-exchange chromatography on a column of CM-cellulose (CM-52, from Whatman Chemical Separations Inc., Clifton, NJ) in 10 mM sodium phosphate buffer, pH 6.0, containing glycine (50 mM) and sodium azide (0.01% w/v). The column was developed with a gradient of 0 to 100 mM sodium chloride in the same buffer. The purified antibody was dialyzed into phosphate-buffered saline.

Gelonin was purified as described by Stirpe et al., J. Biol. Chem., Vol. 255, 6947–6953 (1980) except that the toxin was subjected to additional purification by gel filtration on a column of Sephadex G-100 fine (Pharmacia Fine Chemicals, Uppsala, Sweden) in phosphate buffered saline.

Formation of the Dithiopyridyl Containing J5 Conjugate

Purified antibody was dissolved (1 mg/ml) in 100 mM sodium phosphate buffer, pH 7.0, containing EDTA (1 mM), and 5.5 μl of a freshly prepared solution of 10 mM SPDP (Pierce Chem. Co., Rockford, IL) in ethanol. was added per mL of antibody solution. The reaction mixture was incubated at 30° C. for 30 min, and then the antibody was dialyzed against 100 mM odium phosphate buffer, pH 7.0, containing EDTA (1 mM), to remove excess reagent. About 2 groups are incorporated per antibody molecule to form the dithiopyridyl-containing J5 conjugate under these conditions.

Formation of the Sulfhydryl Containing Gelonin Conjugate

Gelonin at 4 mg/ml in phosphate buffered saline was diluted to 2 mg/ml with distilled water, 0.5 M triethanolamine/HCl buffer, pH 8.0, and 0.1 M EDTA so that the final concentration of triethanolamine and of EDTA were 60 mM and 1 mM, respectively. The solution was degassed and held under argon at 0° C. 2 Iminothiolane hydrochloride (Pierce Chem. Co.) was dissolved at 0.5 M with an ice-cold mixture of 0.5 M triethanolamine/HCl buffer, pH 8.0, and 1.0 M NaOH (1:1 v/v), and 2 μl were added per mL to the ice cold gelonin solution. After incubation at 0° C. for 90 minutes under argon the solution was desalted on a Sephadex G-25 (fine) column in 5 mM bis Tris acetate buffer, pH 5.8, containing NaCl (50 mM) and EDTA (1 mM), in order to remove unreacted reagent and provide the gelonin derivative. This step and all subsequent steps were done at 4° C.

Formation of Immunotoxin

The dithiopyridyl containing J5 conjugate described above (0.5–1.0 mg/ml) in 100 mM NaP$_i$ buffer, pH 7.0, containing EDTA (0.5 mM), was mixed with an equal weight (about a 5-fold molar excess) of the above described sulfhydryl-containing gelonin conjugate (0.5–1.0 mg/ml) in 5 mM bis tris/acetate buffer, pH 5.8, containing NaCl (50 mM) and EDTA (1 mM). The pH of the mixture was raised to 7.0 by the addition of 0.5 M triethanolamine/HCl buffer, pH 8.0, and the mixture was then held under argon at 4° C. for 20 hour. Finally, iodoacetamide (2 mM) was added to block remaining free sulfhydryl groups and incubation continued for an additional hour at 25° C.

Purification of the Immunotoxin

Non-conjugated gelonin as well as the sulfhydryl containing gelonin conjugate were removed from the mixture by passage of the solution through a column of Protein A-Sepharose CL-4B (15 ml column for 100 mg antibody) as described above. The bound protein was eluted with 0.1 M acetic acid containing NaCl (0.15 M) and 0.1 vol of 1.0 M KP$_i$ buffer, pH 7.5, was added to each fraction immediately after collection. The protein was dialyzed against 5 mM NaP$_i$ buffer, pH 6.5, containing NaCl (35 mM) and NaN (0.4 mM) and was then applied to a column of CM cellulose (Whatman, CM-52; 30 ml column for 100 mg antibody) which had been equilibrated with the same buffer. Non-conjugated J5 and its dithiopyridyl-containing conjugate do not bind to CM cellulose under these precise conditions of ionic strength and pH, and were removed from the column by washing with buffer. The J5-containing and gelonin containing immunotoxin was bound by the column and was eluted in a small volume with 100 mM NaP$_i$ buffer, pH 6.5, containing NaCl (1.0 M). It was now free of both non conjugated J5 and gelonin and their conjugates, and was subjected to gel filtration on a column of Sephacryl S-300 (99 cm × 2.6 cm) equilibrated with 10 mM KP$_i$ buffer, pH 7.0, containing NaCl (145 mM) in order to remove aggregates of high molecular weight. The immunotoxin was finally sterilized by passage of the solution through a 0.22 μm filtration membrane (Millex-GV., Millipore Corporation, Bedford, MA).

EXAMPLES 2–5

Monoclonal antibodies I-2, J30, anti-T11$_{1B}$ and anti-T11$_{1C}$ were purified from ascites fluid by affinity chromatography on Protein A-Sepharose CL-4B as described by Goding, J. Immunol, Meth. Vol. 13, 215–226 (1976). Antibody-containing fractions were immediately neutralized by the addition of one tenth volume of 1.0 M NaHCO$_3$, and were then dialyzed against 10 mM NaP$_i$ buffer, pH 6.0, containing glycine (50 mM) and NaN, (0.4 mM), for further purification by ion exchange chromatography on columns of CM cellulose (Whatman, CM-52) equilibrated in the same buffer. The columns (30 ml bed volume for 120 mg of protein) were developed with gradients of NaCl in the same buffer; 0–200 mM for I-2, anti-T11$_{1B}$ and anti-T11$_{1C}$, and 0–300 mM for J30. The purified antibodies were finally dialyzed against 10 mM KP$_i$ buffer, pH 7.2, containing NaCl (145 mM) and stored at −70° C.

Immunotoxins were prepared from I-2, J30, anti-T11$_{1B}$, and anti-T11$_{1C}$, and gelonin, the procedures differing from that of Example I only in the solutions used for the separation of non-conjugated antibody from immunotoxin using CM cellulose. All four buffers for the separation contained NaP (5 mM) and NaN$_3$ (0.4 mM) and were adjusted to pH 6.5, except for the buffer for J30 which was pH 7.0. The concentration of NaCl was 40 mM in the solutions for I-2 and J-30, 34 mM in the solutions for anti-T11$_{1C}$, and 25 mM in the solutions for anti-T11$_{1B}$.

EXAMPLE 6

An immunotoxin was made from anti-T11$_{1A}$ and gelonin by the same procedure as in Example 1 except that since anti-T11$_{1A}$ does not bind to Protein A, ascites fluid containing this antibody was purified by passing it through protein A Sepharose CL-4B to remove traces of murine immunoglobulins that do bind to protein A. The eluate was then fractionated by adding (NH$_4$)$_2$SO$_4$ to 50% saturation. The precipitated protein was dissolved in 10 mM KP$_i$ buffer, pH 7.2, containing NaCl (145 mM), and then dialyzed into the pH 6.0 buffer for chromatography on a column of CM-cellulose as described above: the column was developed with a gradient of 0–300 mM NaCl. Fractions containing anti-T11$_{1A}$ were pooled, concentrated and submitted to gel filtration on a column (99 cm×2.6 cm) of Sephacryl S-300 equilibrated in 10 mM KP$_i$, pH 7.2, containing NaCl (145 mM).

Following cross-linking of this anti-T11$_{1A}$ antibody with gelonin by the procedure described in Example 1, the reaction mixture was concentrated by ultrafiltration, and the excess free gelonin as well as gelonin conjugate and aggregates of high molecular weight were separated by gel filtration on a column (99 cm×2.5 cm, for a 12 ml sample containing 100 mg of antibody) of Sephacryl S-300 equilibrated with 10 mM KP$_i$ buffer, pH 7.2, containing NaCl (145 mM). Free anti-T11$_{1A}$ and its dithiopyridyl-containing conjugate were separated from the immunotoxin by CM-cellulose fractionation as described in Example I except that the buffer was 5 mM NaP buffer, pH 6.5, containing NaCl (21.5 mM) and NaN$_3$ (0.4 mM). The purified immunotoxin was eluted from the column as described above and dialyzed into 10 mM KP$_i$ buffer, pH 7.0, containing NaCl (145 mM).

EXAMPLES 7–11

Immunotoxins were prepared from J5 and each of purified PAP, PAP II and PAP-S following the same procedures as in Example 1. In addition, immunotoxins were made from anti-T11$_{1B}$ and PAP-S by the same procedure as in Example 4, and from anti-T11$_{1A}$ and PAP-S by the same procedure as in Example 6.

Antigen-Binding Activity of Antibodies and Immunotoxins

The binding activity of the various antibodies and of the immunotoxins was measured by indirect immunofluorescence. Cultures of various cells (1×10$^6$) bearing the relevant antigen were incubated at 0° C. for 30 min with serial dilutions of antibody or immunotoxin in 100 μl of Eagle's Minimum Essential Medium for suspension cultures (Gibco Laboratories) supplemented with 2.5% (v/v) pooled human serum of AB-type and 1% (v/v), 1 M HEPES buffer, pH 7.2, containing NaCl (0.9% w/v). The cells were then washed three times with ice-cold medium before they were stained with fluorescein-labelled goat anti mouse IgG antibody for 30 min at 0° C., using 100μl of a 1:25 dilution of the stock solution (Meloy Laboratories) with medium. The cells were again washed three times with ice-cold medium. The fluorescent antibody-coated cells were finally analyzed on an EPICS IV cell sorter (Coulter Electronics, Hialeah, Fl). The results showed that the binding of the immunotoxin to the relevant antigen-positive cells was the same as that of each corresponding antibody itself; moreover, the immunotoxin exhibited no detectable binding to antigen-negative cells. The specificity and avidity of each antibody was fully maintained in the immunotoxin.

Assay of Protein Synthesis in a Cell-Free System

The inhibitory activity of gelonin or the pokeweed antiviral proteins and of the immunotoxins towards protein synthesis was measured in a rabbit reticulocyte lysate system. One microliter samples of gelonin or immunotoxin, diluted to 0.02 μg/ml of gelonin with 10 mM KP$_i$ buffer, pH 7.4, containing NaCl (20 mM) and bovine serum albumin (0.2 mg/ml), were added to the reticulocyte lysate (10μl) in 0.5 ml Eppendorf tubes at 0° C. The reactions were started by the addition of 16μl of a mixture containing salts and buffer cocktail (New England Nuclear), a mixture of 19 amino acids as described previously by Pelham et al., Eur. J. Biochem., Vol. 67, 247–256 (1976), creatine phosphate (0.15μmol), creatine phosphokinase (2.5 μg), mRNA (80 ng), and [$^3$H]-leucine (16 μCi) diluted to a specific radioactivity of 57 mCi/μmol. After rapid mixing, the tubes were incubated at 30° C. Samples (3 μl) were taken at different times and the incorporation of [$^3$H]-leucine into protein was quenched by dilution into distilled water (0.4 ml). Radiolabelled protein was quantified as described by Pelham et al., loc. cit.

Protein synthesis in the foregoing rabbit reticulocyte lysate system was completely inhibited by 20 pg of gelonin. Assay of gelonin conjugate made by reaction with 2-iminothiolane hydrochloride (1.4 thiol groups/mol) after prior reduction with dithioerythritol (20 mM, 30° C. for 30 min.) showed exactly the same inhibition, and it was found that up to 4 thiol groups could be introduced into each gelonin molecule by reaction with 2-iminothiolane hydrochloride without impairing its capacity to inhibit protein synthesis. The J5-gelonin immunotoxin was less active as a protein synthesis inhibitor than native gelonin when assayed without prior reduction, but preincubation with dithioerythritol released fully active gelonin indistinguishable from native gelonin in its ability to inhibit protein synthesis in this assay. Analogous results were obtained with other gelonin immunotoxins as described above as well as with those immunotoxins incorporating PAP, PAP-II and PAP-S.

Cytotoxicity Assay

Cells (0.1 ml of medium, containing 5×10$^4$ cells) were plated into 96-well flat bottom) polystyrene microtiter plates (Microtest III, Becton Dickinson). Equal volumes (0.1 ml of medium, containing serial dilutions of the proteins being tested for cytotoxicity, were added to each well and the cells were then incubated at 37° C. in a SHEL-LAB incubator (Sheldohn MFG Inc., Cornelius, OR), in a humidified atmosphere containing 5% CO$_2$. After the required incubation time, the cells were pulsed for 2 h with [$^3$H]-thymidine (0.8 μCi/well), and then harvested and lysed onto glass fiber discs using a PHD cell harvester (Cambridge Technology, Inc., Cambridge, MA). The radioactivity that was retained on the filters after washing with water and ethanol was measured in 2 ml of Betafluor using a Packard Tri Carb 4530 scintillation counter. All assays were done in triplicate and each experiment was repeated at least 3 times. Values of ID$_{50}$ were estimated as the concentration of immunotoxin that caused 50% inhibition of [$^3$H]-thymidine incorporation.

The foregoing assay was used to test cytotoxicity of the immunotoxins, and all were found to be potent inhibitors of the growth of CALLA bearing cell lines, the onset of toxicity appearing after 2–3 days exposure of the cells.

What is claimed is:

1. An immunotoxin having the structure

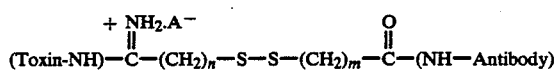

wherein Toxin-NH is gelonin, n is an integer from 1 to 5, m is an integer from 1 to 5, NH-Antibody is a monoclonal antibody specific to eucaryotic cells or to antigens associated therewith, and A$^-$ is a non-toxic water-soluble anion.

2. An immunotoxin as claimed in claim 1 in which said antibody is specific to mammalian cells.

3. An immunotoxin as claimed in claim 1 in which said monoclonal antibody is specific to human T-cells or to common acute lymphoblastic leukemia antigen.

4. An immunotoxin as claimed in claim 1 in which n is 3 and m is 2.

5. An immunotoxin as claimed in claim 4 in which said monoclonal antibody is specific to human T-cells or to common acute lymphoblastic leukemia antigen.

6. An immunotoxin as claimed in claim 4 in which said monoclonal antibody is specific to human T-cells or to common acute lymphoblastic leukemia antigen.

7. The method of making an immunotoxin as claimed in claim 1 which comprises reacting a ribosome-inactivating protein containing no accessible sulfhydryl groups in aqueous medium with an iminothiolester salt having the structure

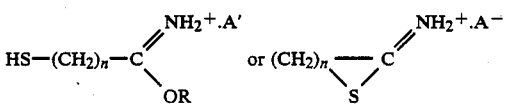

in which n is an integer from 1 to 5, R is an alkyl group having 1 to 5 carbon atoms, and A$^-$ is a water-soluble anion to form a first conjugate having the structure

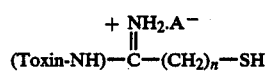

wherein Toxin-NH is gelonin reacting said antibody in aqueous medium with a reagent having the structure

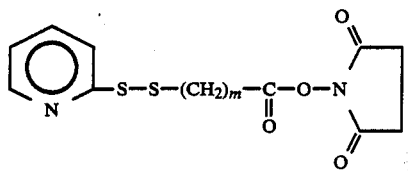

in which m is an integer from 1 to 5 to form a second conjugate having the structure

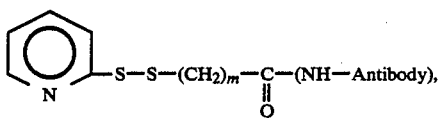

and reacting said first and second conjugates with each other in aqueous medium to form said immunotoxin.

8. The method as claimed in claim 7 in which said iminothiolester salt is 2-iminothiolane hydrochloride and n is 3, and in which m is 2.

9. The method as claimed in claim 7 in which said monoclonal antibody is specific to human T-cells or to common acute lymphoblastic leukemia antigen.

10. The method as claimed in claim 8 in which said monoclonal antibody is specific to human T-cells or to common acute lymphoblastic leukemia antigen.

* * * * *

UNITED STATES PATENT AND TRADEMARK OFFICE
CERTIFICATE OF CORRECTION

PATENT NO. : 4,888,415

DATED : December 19, 1989

INVENTOR(S) : John M. Lambert; Walter A. Blattler; Peter D. Senter

It is certified that error appears in the above-identified patent and that said Letters Patent is hereby corrected as shown below:

Col. 6, line 6     "NaP," should be --NaP$_i$--.
Col. 6, line 28    "NaP" should be --NaP$_i$--.
Col. 6, line 38    "NaP," should be --NaP$_i$--.
Col. 6, line 57    "NaP" should be --NaP$_i$--.
Col. 6, line 58    "NaN," should be --NaN$_3$--.
Col. 7, line 4     "NaP" should be --NaP$_i$--.
Col. 7, line 4     "NaN" should be --NaN3--.
Col. 7, line 40    "NaP" should be --NaP$_i$--.

Signed and Sealed this

Second Day of April, 1991

Attest:

HARRY F. MANBECK, JR.

Attesting Officer

Commissioner of Patents and Trademarks